(12) United States Patent
Hedman

(10) Patent No.: US 8,852,501 B2
(45) Date of Patent: *Oct. 7, 2014

(54) METHOD FOR REMOVING OR TREATING HARMFUL BIOLOGICAL AND CHEMICAL SUBSTANCES WITHIN STRUCTURES AND ENCLOSURES

(75) Inventor: David E. Hedman, Ojai, CA (US)

(73) Assignee: ThermaPure, Inc., Ojai, CA (US)

(*) Notice: Subject to any disclaimer, the term of this patent is extended or adjusted under 35 U.S.C. 154(b) by 783 days.

This patent is subject to a terminal disclaimer.

(21) Appl. No.: 13/104,356

(22) Filed: May 10, 2011

(65) Prior Publication Data
US 2011/0219665 A1    Sep. 15, 2011

Related U.S. Application Data

(63) Continuation of application No. 11/122,579, filed on May 4, 2005, now Pat. No. 8,256,135.

(51) Int. Cl.
| | | |
|---|---|---|
| A61L 2/00 | (2006.01) |
| A01M 1/24 | (2006.01) |
| A61L 2/02 | (2006.01) |
| F24F 3/16 | (2006.01) |
| A01M 19/00 | (2006.01) |
| A61L 2/04 | (2006.01) |
| A01M 1/20 | (2006.01) |
| A61L 9/16 | (2006.01) |
| A01M 21/04 | (2006.01) |
| F23G 7/06 | (2006.01) |
| A61L 2/22 | (2006.01) |
| F24F 11/00 | (2006.01) |

(52) U.S. Cl.
CPC ....... *A01M 1/2094* (2013.01); *A01M 2200/011* (2013.01); *A61L 2/02* (2013.01); *F24F 3/16* (2013.01); *A01M 19/00* (2013.01); *F24F 2003/1664* (2013.01); *A61L 2/04* (2013.01); *A01M 2200/012* (2013.01); *B01D 2257/91* (2013.01); *B01D 2257/90* (2013.01); *A61L 9/16* (2013.01); *F24F 2011/0005* (2013.01); *A01M 21/04* (2013.01); *A01M 1/24* (2013.01); *B01D 2257/2064* (2013.01); *F23G 7/06* (2013.01); *A61L 2/22* (2013.01)
USPC .............................................. 422/22; 43/124

(58) Field of Classification Search
CPC ............................... A01N 25/12; A01M 1/20
USPC .............................................. 422/22; 43/124
See application file for complete search history.

(56) References Cited

U.S. PATENT DOCUMENTS

| 919,827 A | 4/1909 | Cochrane |
| 923,368 A | 6/1909 | Myser |

(Continued)

FOREIGN PATENT DOCUMENTS

| CA | 2205673 | 11/1998 |
| DE | 33 38 848 A1 | 5/1985 |

(Continued)

OTHER PUBLICATIONS

Walter Ebeling, "Expanded Use of Thermal Pest Eradication (TPE)", article, 1997, pp. 1-8, vol. 19, No. 8, the IPM Practitioner, USA.

(Continued)

*Primary Examiner* — Kevin Joyner
(74) *Attorney, Agent, or Firm* — Kelly & Kelley, LLP (57) ABSTRACT

A process for removing or treating harmful biological and chemical substances from an enclosure, such as a building or vehicle by using heated air. The method of the present invention is non-toxic and can be performed in a relatively short amount of time while effectively killing and removing a large proportion of dead organisms and substantially reducing volatile organic compounds.

14 Claims, 7 Drawing Sheets

(56) References Cited

U.S. PATENT DOCUMENTS

| | | |
|---|---|---|
| 1,885,854 A | 11/1932 | Montellano |
| 1,943,613 A | 1/1934 | Lewis |
| 1,948,228 A | 2/1934 | Urban |
| 2,040,110 A | 5/1936 | Tahvonen et al. |
| 2,114,494 A | 4/1938 | Hummel et al. |
| 2,171,315 A | 8/1939 | Renner-felt |
| 2,318,820 A | 5/1943 | Voigt et al. |
| 2,386,676 A | 10/1945 | French |
| 2,606,440 A | 8/1952 | Willey |
| 3,107,974 A | 10/1963 | Potapenko |
| 3,265,862 A | 8/1966 | Smith, Jr. et al. |
| 3,420,439 A | 1/1969 | Meckler |
| 3,748,803 A | 7/1973 | Widerby et al. |
| 3,750,327 A | 8/1973 | Thybault |
| 3,831,332 A | 8/1974 | Weese |
| 3,846,072 A | 11/1974 | Patterson |
| 3,964,268 A | 6/1976 | DiPeri |
| 3,966,407 A | 6/1976 | Zuckerberg et al. |
| 4,045,880 A | 9/1977 | Steffen |
| 4,205,381 A | 5/1980 | Games et al. |
| 4,277,926 A | 7/1981 | Sherman et al. |
| 4,597,192 A | 7/1986 | Sfondrini et al. |
| 4,625,432 A | 12/1986 | Baltes |
| 4,676,152 A | 6/1987 | Tsuji et al. |
| 4,682,424 A | 7/1987 | Irving |
| 4,817,329 A | 4/1989 | Forbes |
| 4,823,520 A | 4/1989 | Ebeling et al. |
| 4,864,942 A | 9/1989 | Fochtman et al. |
| 4,902,315 A | 2/1990 | Spicer |
| 4,918,857 A | 4/1990 | Wade et al. |
| 4,953,320 A | 9/1990 | Nelson |
| 4,955,146 A | 9/1990 | Bollinger |
| 4,958,456 A | 9/1990 | Chaudoin |
| 4,961,283 A | 10/1990 | Forbes |
| 4,989,363 A | 2/1991 | Doernemann |
| 5,022,165 A | 6/1991 | Beswick |
| 5,030,423 A | 7/1991 | Obee et al. |
| 5,058,313 A | 10/1991 | Tallon |
| 5,069,618 A | 12/1991 | Nieberding |
| 5,090,972 A | 2/1992 | Eller et al. |
| 5,096,474 A | 3/1992 | Miller, Jr. et al. |
| 5,109,916 A | 5/1992 | Thompson |
| 5,120,512 A | 6/1992 | Masuda |
| 5,152,077 A | 10/1992 | Liang |
| 5,155,924 A | 10/1992 | Smith |
| 5,192,343 A | 3/1993 | Henry |
| 5,203,108 A | 4/1993 | Washburn, Jr. |
| 5,219,226 A | 6/1993 | James |
| 5,225,167 A | 7/1993 | Wetzel |
| 5,226,244 A | 7/1993 | Carter et al. |
| 5,244,480 A | 9/1993 | Henry |
| 5,293,700 A | 3/1994 | Ishii |
| 5,349,778 A | 9/1994 | Chu |
| 5,369,892 A | 12/1994 | Dhaemers |
| 5,378,086 A | 1/1995 | Campbell, Jr. et al. |
| 5,387,403 A | 2/1995 | Ikeuchi et al. |
| 5,396,729 A | 3/1995 | Vejvoda |
| 5,416,727 A | 5/1995 | Shook et al. |
| 5,442,876 A | 8/1995 | Pederson |
| 5,491,092 A | 2/1996 | Colvin |
| 5,556,607 A | 9/1996 | Childers et al. |
| 5,590,478 A | 1/1997 | Furness |
| 5,590,830 A | 1/1997 | Kettler et al. |
| 5,612,001 A | 3/1997 | Matschke |
| 5,761,908 A | 6/1998 | Oas et al. |
| 5,768,907 A | 6/1998 | Lee |
| 5,806,238 A | 9/1998 | Brenner |
| 5,837,040 A | 11/1998 | Caughron et al. |
| 5,874,050 A | 2/1999 | Matias |
| 5,960,556 A | 10/1999 | Jansen |
| 5,960,558 A | 10/1999 | Bourgault |
| 5,979,472 A | 11/1999 | Lowery et al. |
| 6,032,474 A | 3/2000 | Dale et al. |
| 6,141,901 A | 11/2000 | Johnson et al. |
| 6,161,327 A | 12/2000 | Thomas |
| 6,162,393 A | 12/2000 | De Bruiju et al. |
| 6,199,770 B1 | 3/2001 | King et al. |
| 6,279,261 B1 | 8/2001 | Binker et al. |
| 6,289,974 B1 | 9/2001 | De Gregoria |
| 6,327,812 B1 | 12/2001 | Hedman et al. |
| 6,383,449 B1 | 5/2002 | Pennekamp et al. |
| 6,451,152 B1 | 9/2002 | Holmes et al. |
| 6,494,934 B2 | 12/2002 | Fukushima |
| 6,612,067 B2 | 9/2003 | Topp |
| 6,656,424 B1 | 12/2003 | Deal |
| 6,878,177 B2 | 4/2005 | Lohr et al. |
| 6,892,491 B2 | 5/2005 | Hedman |
| 6,911,177 B2 | 6/2005 | Deal |
| 6,962,619 B1 | 11/2005 | DeRosa et al. |
| 7,271,706 B2 | 9/2007 | Lee |
| 7,690,148 B2 | 4/2010 | Hedman |
| 2003/0100465 A1 | 5/2003 | Kilkenny et al. |
| 2003/0230477 A1 | 12/2003 | Fink et al. |
| 2004/0028554 A1 | 2/2004 | Hedman |
| 2007/0140893 A1* | 6/2007 | McVey et al. ............... 422/3 |

FOREIGN PATENT DOCUMENTS

| | | |
|---|---|---|
| DE | 3421719 A1 | 12/1985 |
| DE | 40 25 828 A1 | 2/1992 |
| DE | 42 05 459 A1 | 8/1993 |
| DE | 43 08 585 A1 | 9/1994 |
| EP | 0 676 138 A1 | 8/1997 |
| JP | 2187115 A | 7/1990 |
| JP | 2000116757 A | 4/2000 |
| WO | 01/91858 A1 | 12/2001 |

OTHER PUBLICATIONS

Charles Forbes and Walter Ebeling, "Use of Heat for Elimination of Structural Pests", article, 1987, pp. 1-5, vol. 9, no. 8, the IPM Practitioner, USA.

Walter Ebeling, Charles F. Forbes and Sandra Ebeling, "Heat Treatment for Powderpost Beetles", article, 1989, pp. 1-4, vol. 11, No. 9, the IPM Practitioner, USA.

William Ebeling, "The Thermal Pest Eradication System for Structural Pest Control", article, 1994, pp. 1-7, vol. 16, No. 2, the IPM Practitioner, USA.

(Unknown), "Guidelines on Assessment and Remediation of Stachybotrys Atra in Indoor Environments", based on panel discussion, 11 pages, 1993, New York, NY, USA.

P.R. Morey, "Microbiological Contamination in Buildings: Precautions During Remediation Activities", article, pp. 171-178, Clayton Environmental Consultants, USA.

Eckard Johanning, Philip R. Morey and Mark Goldberg, "Remedial Techniques and Medical Surveillance Program for the Handling of Toxigenic Stachybotrys Atra", article, 1993, vol. 4, pp. 311-316, Proceedings of Indoor Air, USA.

Pete Consigli, "Contaminated Crawl Spaces: the Good, the Bad, and the Ugly", symposium, 1996, 6 pp., ASCR 50th Convention, USA.

(Unknown), "Environmental Report #1", report, 1996, 9 pages, Safe Environments Home & Office Testing Services, USA.

James E. Holland and John Banta, "Developing Protocols and Technical Specifications: Chapter 1—Introduction", book, 1998, 10 pages, Restoration Hygiene Institute, USA.

James E. Holland, "Developing Protocols and Technical Specifications: Chapter 2—Project Planning", book, 1998, 8 pages, Restoration Hygiene Institute, USA.

James E. Holland, "Developing Protocols and Technical Specifications: Chapter 3—Containment Strategy", book, 1998, 32 pages, Restoration Hygiene Institute, USA.

James E. Holland, "Developing Protocols and Technical Specifications: Chapter 4—Safety Issues", book, 1998, 9 pages, Restoration Hygiene Institute, USA.

James E. Holland, "Developing Protocols and Technical Specifications: Chapter 5—Job Set Up Work Area Preparation", book, 1998, 28 pages, Restoration Hygiene Institute, USA.

James E. Holland, "Developing Protocols and Technical Specifications: Chapter 6—Work Procedures", book, 1998, 39 pages, Restoration Hygiene Institute, USA.

(56) References Cited

OTHER PUBLICATIONS

James E. Holland, "Developing Protocols and Technical Specifications: Chapter 7", book, 1998, 5 pages, Restoration Hygiene Institute, USA.

David Bierman, "Microbial Contamination", report, 12 pages, Safe Environments Home & Office Testing Services, USA.

Joseph W. Lstiburek, "Mold, Moisture & Indoor Air Quality: A Guide for Designers, Builders, and Building Owners—Introduction", book, 1994, 14 pages, Building Science Corporation, USA.

Joseph W. Lstiburek, "Mold, Moisture & Indoor Air Quality: A Guide for Designers, Builders, and Building Owners—Chapter 1: People, Buildings, and the Environment", book, 1994, pp. 7-20, Building Science Corporation, USA.

Joseph W. Lstiburek, "Mold, Moisture & Indoor Air Quality: A Guide for Designers, Builders, and Building Owners—Chapter 2: HVAC Systems and Air Quality Problems", book, 1994, pp. 21-50, Building Science Corporation, USA.

Joseph W. Lstiburek, "Mold, Moisture & Indoor Air Quality: A Guide for Designers, Builders, and Building Owners—Chapter 3: Moisture Movement and Relative Humidity", book, 1994, pp. 51-62, Building Science Corporation, USA.

Joseph W. Lstiburek, "Mold, Moisture & Indoor Air Quality: A Guide for Designers, Builders, and Building Owners—Chapter 4: Microbial Contamination", book, 1994, pp. 63-68, Building Science Corporation, USA.

Joseph W. Lstiburek, "Mold, Moisture & Indoor Air Quality: A Guide for Designers, Builders, and Building Owners—Chapter 5: Cold Climate Mold, Mildew and Condensation", book, 1994, pp. 69-82, Building Science Corporation, USA.

Joseph W. Lstiburek, "Mold, Moisture & Indoor Air Quality: A Guide for Designers, Builders, and Building Owners—Chapter 6: Warm Climate Mold, Mildew and Condensation", book, 1994, pp. 83-112, Building Science Corporation, USA.

Joseph W. Lstiburek, "Mold, Moisture & Indoor Air Quality: A Guide for Designers, Builders, and Building Owners—Chapter 7: Vapor Diffusion Retarders, Air Retarders and Insulating Sheathings", book, 1994, pp. 113-128, Building Science Corporation, USA.

Joseph W. Lstiburek, "Mold, Moisture & Indoor Air Quality: A Guide for Designers, Builders, and Building Owners—Chapter 8: Case Studies", book, 1994, pp. 129-244, Building Science Corporation, USA.

Michael A. Berry, "Protecting the Built Environment: Cleaning for Health", book, 1993, 84 pages, Tricomm 21st Press, USA.

(Unknown), "Ashrae Handbook: 1983 Equipment Volume", handbook, 1983, 78 pages, American Society of Heating, Refrigerating and Air-Conditioning Engineers, Inc., USA.

(Unknown), "1996 Ashrae Handbook: Heating, Ventilating, and Air-Conditioning—Systems and Equipment", handbook, 1996, 194 pp., American Society of Heating, Refrigerating and Air-Conditioning Engineers, Inc., USA.

(Unknown), "Ashrae Handbook: 1982 Applications", handbook, 1982, 84 pages, American Society of Heating, Refrigerating and Air-Conditioning Engineers, Inc., USA.

(Unknown), "Ashrae Handbook: 1984 Systems", handbook, 1984, 104 pages, American Society of Heating, Refrigerating and Air-Conditioning Engineers, Inc., USA.

(Unknown), "1995 Ashrae Handbook: Heating, Ventilating, and Air-Conditioning Applications", handbook, 1995, 232 pages, American Society of Heating, Refrigerating and Air-Conditioning Engineers, Inc., USA.

(Unknown), "The Dehumidification Handbook", handbook, 1982, 67 pages, The Cargocaire Engineering Corporation, USA.

(Unknown), "The Dehumidification Handbook", handbook, 1990, 2nd Ed., 153 pages, Munters Cargocaire, USA.

(Unknown), "Design Considerations for Toxic Chemical and Explosives Facilities", symposium, 1987, 33 pages, American Chemical Society, USA.

Seymour S. Block, "Disinfection, Sterilization, and Preservation", 3rd Ed, book, 1983, 160 pages, Lea & Febiger, Philadelphia, PA, USA.

W.A. Murray, A.J. Streifel, T.J. O'Dea, F.S. Rhame, "Ventilation for Protection of Immune Compromised Patients", journal, 1988, pp. 1185-1191, vol. 94, USA.

John R. Girman, Leon E. Alevantis, George C. Kulasingam, Myrto X. Petreas, and Lurance M. Webber, "The Bake-Out of an Office Building: A Case Study", study, 1989, Environmental International, vol. 15, pp. 449-453, Pergamon Press, USA.

Ernie Storrer, "Mold & Trapped Moisture", article, 1997, 2 pages, Cleaning and Restoration, Injectidry Systems, Inc., USA.

(Unknown), "Structural Drying School Handbook", handbook, pp. 1-82, American Drying Institute, USA.

Chuck Dewald, "Chuck Dewald's Vortex Drying System School Study Guide", handbook, pp. 1-10, Vortex Drying System, USA.

(Unknown), "The Mobile Hands-On' Water Damage Restoration Technician School: Interactive Student Manual", manual, 2000, 292 pages, Aspire Educational Institute & Conference Centre, Costa Group, Inc., USA.

Clifford B. Ziotnik, "Microban Systems, Inc. Water Restoration Technology Manual", manual, 2002, 96 pages, Microban Systems, Inc., USA.

Michael A. Pinto and David Janke, "Fungal Contamination: A Comprehensive Guide for Remediation", handbook, 2001, 329 pages, Wonder Makers Environmental, Inc., USA.

Bill Lundquist et al., "Assessment, Cleaning, and Restoration of HVAC Systems", manual, 2006, 52 pages, National Air Duct Cleaners Association (NADCA), USA.

(Unknown), "A Brief Guide to Mold in the Workplace", bulletin, 2010, 51 pages, Office of Science and Technology Assessment, USA.

(Unknown), "Mold Remediation in Schools and Commercial Buildings", manual, 2001, 70 pages, U.S. Environmental Protection Agency, USA.

Joseph A. Hughes, "Indoor Environmental Contractor Program: Microbial Remediation Supervisor", manual, 2003, 231 pages, IAQ Training Institute LLC, USA.

William Quarles, "Thermal Pest Eradication in Structures", newsletter, 2006, 8 pages, vol. 28, Issue 5/6, The IPM Practitioner, USA.

George A. Dean, "Further Data on Heat as a Means of Controlling Mill Insects", journal, 1913, pp. 40-55, vol. 6, Journal of Economic Entomology Publishing Co., USA.

(Unknown), "Standard and Reference Guide for Professional Water Damage Restoration (IICRC S500)", manual, 1994, 360 pages, Institute of Inspection, Cleaning and Restoration (IICRC), USA.

(Unknown), "Standard and Reference Guide for Professional Mold Remediation (IICRC S520)", manual, 2003, 239 pages, Institute of Inspection, Cleaning and Restoration (IICRS), USA.

(Unknown), "Electric Thermal Energy System Operator's Manual (120 Volt)", manual, 2010, 44 pages, Bridgepoint Systems, USA.

(Unknown), "Electric Thermal Energy System Operator's Manual (240 Volt)", manual, 2009, pp. 1-4, 7-39, Bridgepoint Systems, USA.

(Unknown), "Atlas Owner's Manual & Parts List", manual, 2008, 14 pages, EDIC, USA.

Michael D. Geyer, "Benefits of Dry Heat to Clean Structures of Biological Contamination and Improve Indoor Air Quality (IAQ)", article, 2002, 6 pages, SCS Engineers, USA.

Alan Forbess, "Turning Up the Heat: New Remediation Process for Water Damage Could Save Insurers 'Billions'", magazine, 2006, pp. 46 & 48, Canadian Underwriter, Canada.

Alan Forbess, "Heat Treatment Method Provides Water Damage/Mold Relief", journal, 2006, 3 pages, vol. 54, No. 5, Claims, USA.

Michael Geyer, "Mold Remediation with Heat", magazine, 2006, 3 pages, ICS Cleaning Specialist, USA.

(Unknown), "Project Watch: New Weapons in the War Against Mold", magazine, 2006, 4 pages, Multifamily Trends, USA.

Megan Headley, "Some Like It Hot: How Heat Has Become a Tool for Mold Remediation", magazine, 2006, pp. 20-22 & 24, Mold & Moisture Management Magazine, Key Communications, Inc., USA.

Mike Geyer, "Structural Pasteurization: Mold Remediation With Heat", magazine, 2006, 4 pages, Building Services Management, USA.

(Unknown), "New Heat Treatment Process Used for Mold Removal", website, 2006, pp. 1-3, www.tradelineinc.com, USA.

(56) References Cited

OTHER PUBLICATIONS

Michael D. Geyer, "Benefits of Dry Heat to Clean Structures of Biological Contamination and Improve Indoor Air Quality (IAQ)", website, pp. 1-9, Precision Environmental, Inc., www.precisionenv.com, USA.
(Unknown), "Stop Mold With Heat", website, pp. 1-2, Precision Environmental, Inc., www.precisionenv.com, USA.
Joe McLean, "The Facts About Mold and Indoor Air Quality Using the New 'ThermaPure' Heat Treatment: Guide for Property Managers", manual, 2007, pp. 1-15, Alliance-Environmental Group, Inc. (Joe McLean), USA.
(Unknown), "Moisture Control, Mold, and the Science Within the Building Envelope", website, 2006, pp. 1-4, www.amazon.com, USA.
(Unknown), "Heat—Another Effective Tool in Your Pest Control Toolbox", manual, 148 pages, Thermal Remediation from TempAir, USA.
Anthony Manton, "Complex Solutions Made Simple", manual, 1988, pp. 1-49, Deep Sea Electronics PLC, UK.
(Unknown), "Operation Manual for EBB-40KW Trailer Package", manual, pp. 1-8, Thermal Remediation from TempAir, USA.
(Unknonwn), "Thermal Pest Management Chamber for Heat Treatment (H.T.) Process", website, 2001, 5 pages, www.pestheat.com, Pest-Heat, USA.
(Unknown), "Bed Bug: Heat Treatment Equipment and Application Training", manual, 12 pages, Thermal Remediation from TempAir, USA.
(Unknown), "EBB-115V Hotel Package", catalog, 2 pages, Thermal Remediation from TempAir, USA.
(Unknown), "Thermal Remediation Pest Control Training Course", manual, 2010, pp. 1-24, Temp-Air, USA.
Michael R. Linford and William Currie, "Bedbugs Put the Bite on Hotel Business", article, 2006, 3 pages, Asian American Hotel Owners Association, USA.
Lisa Lupo, "Treating With Heat", article, 2008, 4 pages, Pest Management, USA.
(Unknown), "Benefits of Being a ThermaPureHeat Licensee", handbook, 2005, pp. 1-39, E-Therm, Inc., USA.
Ole Dosland, Bhadriraju Subramanyam, Ken Sheppard and Rizana Mahroof, "Temperature Modification for Insect Control", book, pp. 89-102, Chapter 10 of Insect Management for Food Storage and Processing, AACC International, USA.
(Unknown), "ThermaPure, Inc. Receives New U.S. Patent for the Use of Heat Technology for Bed Bugs", 2010, article, 2 pages, ThermaPure, Inc., USA.
(Unknown), "Aggreko Heats Up the Food Industry", article, 1999, 1 page, Aggreko Inc., USA.
Alan K. Dowdy and Paul G. Fields, "Heat Combined with Diatomaceous Earth to Control the Confused Flour Beetle (Coleoptera: Tenebrionidae) in a Flour Mill", journal, 2002, pp. 11-22, Journal of Stored Products Research 38, Elsevier Science Ltd., USA.
Bhadriraju Subramanyam and David W. Hagstrum, "Inert Dusts", book, 2000, pp. 321-380, Chapter 12 of Alternatives to Pesticides in Stored-Product IPM, Kluwer Academic Publishers, USA.
Paul G. Fields, "Diatomaceous Earth: Advantages and Limitations", symposium, pp. 781-784, vol. 1, Proceedings of the 7th International Working Conference on Stored-Product Protection, Agriculture and Agri-Food Canada, Cereal Research Centre, Canada.
(Unknown), "Diatomaceous Earth (DE)", website, 2000-2007, 6 pages, The Bluebird Box—Best of Bluebird Mailing Lists Classified, Audubon Society of Omaha, USA.
(Unknown), "Model EBB-115V Thermal Treatment Heater Operator's Manual", manual, pp. 1-15, Thermal Remediation Division, Temp-Air, Inc., USA.
(Unknown), "Model EBB-460 Room Thermal Treatment Heater Operator's Manual", manual, pp. 1-14, Thermal Remediation Division, Temp-Air, Inc., USA.
(Unknown), "Temp-Heat THP-1400, 2000, 3000, 4000 and 4500: Gas, Direct-Fired Temporary Heater Installation and Service Manual", manual, 2007, pp. 1-26, TempAir, Rupp Industries, Inc., USA.
(Unknown), "Temp-Heat THP-500HT: Gas, Direct-Fired Temporary Heater Installation and Service Manual", manual, 2002, pp. 1-17, TempAir, Rupp Industries, Inc., USA.
(Unknown), "Point Sensor Temperature 3006-21 Installation and Operation Instructions", manual, 3 pages, Point Six Wireless, USA.
Albert C. Apt, "A Study of the Role of Vacuum Cleaning in the Control of Insects in Flour Mills", article, 1955, pp. 5-7, vol. 20, No. 8, Milling Production, USA.
(Unknown), "C-2000 Operating Manual", manual, 7 pages, Tri-Dim Filter Corp., USA.
George A. Dean, "Heat As a Means of Controlling Mill Insects", journal, 1913, pp. 142-161, vol. 4, Journal of Economic Entomology, USA.
George A. Dean, "Further Data on Heat as a Means of Controlling Mill Insects", journal, 1911, pp. 40-55, vol. 6, Journal of Economic Entomology, USA.
(Unknown), "Portable Industrial Unit Blower Air Heater Type DRA: Installation, Operation and Renewal Parts Identification", manual, 2002, pp. 1-6, Chromalox, Inc., USA.
(Unknown), "Temp-Heat ETHP-100: Electric Construction Heaters Installation and Service Manual", manual, pp. 1-11, TempAir, Rupp Industries, Inc., USA.
(Unknown), "Temp-Heat ETHP-1500 and ETHP-1500 Electric Construction Heaters Installation and Service Manual", manual, 1998, pp. 1-15, TempAir, Rupp Industries, Inc., USA.
(Unknown), "Remote Monitoring Wireless Sensor Product Families", catalog, 9 pages, Point Six Wireless, LLC, USA.
Walter Ebeling, "Heat and Silica Aerogel are Synergistic", article, pp. 11-12, vol. 16, IPM Practitioner, USA.
Jody Gangloff-Kaufmann and Jill Shultz, "Bed Bugs are Back! An IPM Answer", article, 2003, pp. 1-5, NYS Integrated Pest Management Program, USA.
(Unknown), "What Is Integrated Pest Management", article, 1997, pp. 3-8, Chapter 1, USEPA, Document #909-B-001 by the Bio-Integral Resource Center, USA.
C.L. Marlatt, "The Bedbug", bulletin, 1916, 17 pages, Farmer's Bulletin No. 754, U.S. Department of Agriculture, USA.
(Unknown), "Understanding the TPE Process", manual, 1999, 106 pages.
Mark Mire, "The History of Heat Sterilization for Pest Control", article, 1996, 107 pages, Aggreko, Inc., USA.
(Unknown), "Frequently Asked Questions About Bed Bugs, Their Bites, and How to Kill and Get Rid of Them", website, 2011, 6 pages, ThermaPure, Inc., USA.
George A. Dean, "Heat as a Means of Controlling Mill Insects", Journal, 1911, pp. 142-161, vol. 4, Journal of Economic Entomology Publishing Co., USA.
W.C. O'Kane and W.A. Osgood, "Studies in Termite Control", Bulletin, 1922, pp. 1-20, Bulletin No. 204, New Hampshire College of Agriculture and the Mechanic Arts, USA.
U.S. Department of Agriculture, "Insect Control in Flour Mills", Handbook, 1958, pp. 23-25, Agriculture Handbook No. 133, U.S. Government Printing Office, USA.
(Unknown), "The Way Things Work", 1967, pp. 248-249, 262-265, Simon & Schuster, USA.
R. Elsworth, "Treatment of Process Air for Deep Culture", Book, 1969, pp. 129-135, vol. 1, Chapter 4, Academic Press Inc., London and New York.
David A. Sterling, C. Clark, and S. Bjornson, "The Effect of Air Control Systems on the Indoor Distributions of Viable Particles", Study, 1982, pp. 409-414, Environment International, vol. 8, Pergamon Press, Ltd., USA.
Kenneth O. Sheppard, "Heat Sterilization (Superheating) as a Control for Stored-Grain Pests in a Food Plant", Book, 1984, pp. 193-200, American Association of Cereal Chemists, USA.
Charles Forbes and Walter Ebeling, "Use of Heat for Elimination of Structural Pests", Newsletter, 1987, pp. 1-5, vol. 9, Issue 8, IPM Practitioner, USA.

(56) References Cited

OTHER PUBLICATIONS

Walter Ebeling, Charles F. Forbes and Sandra Ebeling, "Heat Treatment for Powderpost Beetles", Newsletter, 1989, pp. 1-4, vol. 11, Issue 9, IPM Practitioner, USA.
Stewart Brand and Richard Kadrey, "The Chronicle Whole Earth Catalog Briefing: Safe Homes/The Toxic-Free House", Article, 1991, pp. 1-3, San Francisco Chronicle, USA.
David W. Bearg, "Indoor Air Quality and HVAC Systems", Book, 1993, pp. 1-209, CRC Press, USA.
Paul Stamets, "Growing Gourmet and Medicinal Mushrooms", Book, 1993, pp. 171-173, Ten Speed Press, USA.
Walter Ebeling, "The Thermal Pest Eradication System for Structural Pest Control", Newsletter, 1994, pp. 1-7, vol. 16, Issue 2, The IPM Practitioner, USA.
M. Nicholson and W. Von Rotberg, "Controlled Environment Heat Treatment as a Safe and Efficient Method of Pest Control", Symposium, 1996, pp. 263-265, Thermo Lignum UK Ltd., UK.
Lisa G. Neven and Elizabeth J. Mitcham, "CATTS (Controlled Atmosphere/Temperature Treatment System): A Novel Tool for the Development of Quarantine Treatments", Research, 1996, pp. 56-59, American Entomologist, USA.
Jerry Heaps, "Heat for Stored Product Insects", Newsletter, 1996, pp. 18-19, vol. 18, Issues 5-6, The IPM Practitioner, USA.
David Pinniger, "Insect Control With the Thermo Lignum Treatment", Newsletter, 1996, No. 59, Conservation News, UK.
(Unknown), "Dri-Eaz Owner's Manual for Dri-X AirChanger", Manual, 1997, pp. 1-14, Dri-Eaz Products, Inc., USA.
John Gladstone and W. David Bevirt, "HVAC Testing, Adjusting, and Balancing Manual", Manual, 1997, pp. 94-101, 167-169, 172-175, 287-301, Third Edition, McGraw-Hill, USA.
U.S. Army Center for Health Promotion and Preventive Medicine, "Procedures for Thermal Control of Cockroaches in Army Food Service Facilities", Manual, 1997, pp. 1-1 thru H-1, USACHPPM Technical Guide No. 208, U.S. Government, USA.
Walter Ebeling, "Expanded Use of Thermal Pest Eradication (TPE)", Newsletter, 1997, pp. 1-8, vol. 19, Issue 8, The IPM Practitioner, USA.
R. Joseph Woodrow and J. Kenneth Grace, "Cooking Termites in the Aloha State", Article, 1997, pp. 1-3, Advanstar Communications Inc., USA.
Michael K. Rust and Donald A. Reierson, "Temperature Sensitivity in Insects and Application in Integrated Pest Management", Book, 1998, pp. 179-200, Westview Press, USA.
Brian C. Zeichner, Alfred L. Hoch and Donald F. Wood, Jr., "Heat and IPM for Cockroach Control", Newsletter, 1998, pp. 1-6, vol. 20, Issue 2, The IPM Practitioner, USA.
William Quarles, "Pest Control Operators and Heat Treatment", Newsletter, 1994, p. 8, vol. 16, The IPM Practitioner, USA.
Gary L. Servais, "Heat Sterilization Project", Journal, 1996, 60 pp., Brown & Williamson Tobacco Corporation, USA.
William Quarles, "Diatomaceous Earth for Pest Control", article, 1992, 16 pp., vol. XIV, No. 5/6, The IPM Practitioner, USA.
J. Coombs and K.E. Hall, "Dictionary of Biological Control and Integrated Pest Management", dictionary, 1998, 3 pages, CPL Scientific Publishing Services Limited, UK.
David Cain, "In Bed Bugs We Trust Inc. The Bed Bug University Summit", website, 2011, 2 pages, Pest Magazine, UK.
McGregor Pearce, "Mold", article, 50 pages.
Ernie Storrer, "The Drying Pie", article, 8 pages, Injectidry Systems, Inc., USA.
Michael D. Geyer, "Mold Is Not the Problem", article, 5 pages, SCS Engineers, USA.
Mike Geyer, "Mold Remediation With Heat—Does a Better Job!", article, 5 pages, SCS Engineers, USA.
Michael D. Geyer and Kenneth V. La Conde, "Toxic Mold Is Not the Problem", article, pp. 1-5, SCS Engineers, USA.
G.A. Dean, "Heat for Mill Insects," Journal of Economic Entomology, 1913, pp. 40-55, vol. 6, Journal of Economic Entomology Publishing Co., Concord, New Hampshire.

\* cited by examiner

METHOD FOR REMOVING OR TREATING HARMFUL BIOLOGICAL AND CHEMICAL SUBSTANCES WITHIN STRUCTURES AND ENCLOSURES

RELATED APPLICATION

This application is a continuation of U.S. patent application Ser. No. 11/122,579, filed 4 May 2005 (now U.S. Pat. No. 8,256,135).

BACKGROUND OF THE INVENTION

The present invention relates to methods of sanitizing structures, buildings, passenger occupiable vehicles, and other enclosed or enclosable spaces. More particularly, the present invention relates to a method for killing and/or removing pests and their allergens, bacteria, viruses, fungi, molds, volatile organic compounds and other dangerous substances, such as Mercury, from such enclosures.

It is a common problem that pests, such as insects and rodents, find their way into homes, hotels and other structures. For example, mice, rats, and other rodents often find access into a home or building through open doors, crevices, etc., and nest and breed within the house, particularly within the winter months.

The presence of such rodents, or nesting birds or bats, can also introduce other pests into the structure. For example, fleas, lice and beg bugs often find there way into homes, hotels, etc., by transmission of birds and rodents which nest within the eaves or within the structure of the home or hotel. There are at least 70 different kinds of bed bugs across the world. The blood-sucking parasites are wingless, dark reddish-brown, oval and flat insects. Full-size adults are typically less than one quarter inch long, and mature in about four weeks after hatching, if a host is available. Bed bugs can endure freezing temperatures and use a variety of hosts besides humans, including poultry, rodents, dogs, cats, birds and bats. Although humans rarely feel the approximately 15 minute long bite, some people show sensitive reactions to it. An indication of bed bugs is small blood spots on bed sheets. Bed bugs hide in cracks and crevices during the day, and come out at night to feed. They are found around mattresses, behind picture frames, in night stands, stuffed furniture, behind loose wallpaper, and other enclosed spaces. They will crawl a substantial distance to obtain a blood meal. This is particularly a problem in the hotel industry, where customers can pay several hundred dollars a night for their room, and awake in the room with bed bug bites and bloodied sheets.

In desert settings, it is not uncommon for scorpions to infest homes, and occasionally sting unsuspecting adults or curious children or animals. The scorpions gain access to the dwelling through holes or crevices in the house and are attracted to the moisture and cooler temperatures.

A large number of methods have been developed for killing insects, such as termites, in buildings. The most widely used method is tenting the building, then filling the building with a toxic gas for a period of time sufficient to kill termites or other selected insects. This method is effective for killing termites and other insects. However, this method generally requires 12 hours to be effective, requiring building occupants to move out and businesses to be closed for approximately a three day period to insure proper venting of toxic material and/or gas. Tenting the building with heavy tarpaulins requires workers to walk and arrange the tarpaulins on the roof, often damaging the roof system. Food and medications must be placed in sealed containers or removed. Generally the entire building must be treated, even if the infestation is localized.

Techniques of varying effectiveness have been developed using heated air or very cold air to kill termites and other organisms. Typical of these are the methods disclosed by Charles Forbes in U.S. Pat. No. 4,817,329, in which wood destroying insects, e.g., termites, are killed by applying a heated gas, such as heated air, to wooden surfaces or the like until the core of wooden structures is heated to a temperature typically about 120° F. to 135° F. This method has been found to be very effective for killing termites. Another alternative to the toxic gas method is disclosed by James J. Chaudoin, et al. in U.S. Pat. No. 4,958,456, in which insects, e.g., roaches, fleas and beetles, are killed by a treatment of building spaces with boric acid and heat. However, the methods disclosed in the Forbes patent are quite complex in the preparation of the building. An enclosing tent structure must be formed around the building to be decontaminated, as the termites and wood eating insects are typically found in the framing, shingles, and outer panels of the building. Tenting the building with heavy tarpaulins requires workers to walk and arrange the tarpaulins on the roof, often damaging the roof system.

Other organisms, such as bacteria, viruses, fungi, and molds such as, but not limited to, *aspergillus oryzae, aspergillus terreus, aspergillus versicolor, cladosporium hergbarum, stachybotrys chartarum, penicillium aurantiogriseum, pencillium chrsogenum, pencillium gladrum* and *fusarium oxysporum*, are a serious health hazard even when dead. Many people are allergic to the dust-like remains and residue, i.e., allergens, of these organisms that can also cause serious health problems. This is a particular problem to persons suffering from asthma, bronchitis, pneumoconious and other respiratory ailments, and is a common contributing factor to sick building syndrome (SBS).

It is also well-known that the heated air causes certain molds, fungi, etc. to sporulate, thus releasing spores into the structure and thus dispersing the harmful biological agents and possibly contaminating the structure to a greater degree than originally presented. The use of positive pressure within the structure, as described in Forbes and Hedman et al., further increase the likelihood that the biological contaminants will be dispersed throughout the structure. Forbes also discloses that the heated air can be vented from open windows and the like. However, when treating a contaminated building having harmful viruses, toxic molds, etc., it is not desirable to release such contagions into the air.

Volatile organic compounds (VOCs) have also been implicated as a possible cause of SBS. VOCs can originate from a variety of sources. Commercial examples include by-products of printing shop operations, office machine repairs, blueprint production, photographic processing and food service operations. In residences, such VOCs can include hobbyist products, cosmetics, perfumes, personal hygiene products, aerosol sprays, tobacco smoke, pet urine and even small emissions from the bodies of the occupants. Off-gassing of VOCs is often a common by-product of various building/construction materials, for example paints, adhesives, plastics, carpeting, etc.

Such VOCs are implicated with SBS for mostly two reasons. First, the health effects from exposure to VOCs are consistent with SBS, ranging from irritant effects such as unpleasant odors and mucous membrane irritation, through general systemic effects such as fatigue, nausea, and difficulty concentrating. In addition, they may be of importance because some of them have been shown to have carcinogenic or adverse reproductive effects. Second, indoor concentrations of VOCs, particularly in new buildings, are often greatly elevated with respect to outdoor VOC concentrations. In fact, indoor VOC concentrations have typically been found to be two to ten times higher then outdoor concentrations, and indoor concentrations as much as 100 times higher than outdoor concentrations have been reported in new buildings.

In the northeastern parts of the United States, it is common for heating oil to be delivered and used in the heating of the home during the winter months. The oil can spill, and the fuel oil fumes and odors can infiltrate the house over time and contribute to SBS.

Passenger occupiable vehicles, such as trains, buses, airplanes, etc. also include building/construction materials which are known to off-gas VOC's. Also, the fuel, oil, and grease fumes and odors can infiltrate the passenger compartments of such vehicles and build-up within the seats, carpets, etc. over time. Due to the great number of people regularly traveling in such vehicles, there is an increased chance of coming into contact with contagious bacterium or viruses that can cause illness. Other organisms, such as fungi, and toxic molds can also be potentially found in such vehicles. As the company owning such vehicles necessarily must keep the vehicles running nearly constantly in order to realize the expected profit, such vehicles are rarely cleaned thoroughly. Even if the surfaces are superficially vacuumed and wiped down, there still remain live and dead organisms such as lice, mites, fungi, toxic molds, bacterium, viruses, VOCs, oxidized odors, and potentially insects which may have infested the vehicle, particularly those where food is prepared or served.

A common problem in the wine industry is cork taint. This is most accurately described as a "moldy" or "musty" smell that masks or dominates the fruit aroma of wine and reduces the overall wine quality. Infected wines are said to be "corked" or "corky". The causes of cork taint are believed to be two-fold. Molds may be originally present in raw cork bark or in wood used for barrels or other winery equipment or facilities, and can infect cork or wood in storage. Ironically, chemicals which react with the molds are introduced by methods and equipment used for keeping the production environment sterile and safe. One culprit is chlorine bleach used in cork processing and also as a routine disinfectant in wineries. Another is atmospheric off-gassing from plastic equipment. TCA, a common abbreviation for various chloroanisole compounds (such as 2,4,6-trichloroanisole, and 2,3,4,6-tetrachloroanisole), is also thought to be a primary cause of cork taint. Damage to the wine industry annually is estimated to be $10 Billion worldwide. A method is needed to prevent or purge TCA, and other atmospheric pollution and residue bleach, from corks and wooden barrels and structures in the production facilities. Similar problems arising from TCA are known to exist in the food and shipping industries.

When constructing new buildings, such as homes and the like, framed with wooden beams, a growing concern is the moisture content of the wood which can result in toxic-mold. Another problem is that framing lumber that has too high a moisture content may lead to shrinkage, resulting in drywall cracking and other problems in the structure. Such moisture-laden or "green" lumber typically has a moisture content between 19%-28%. In the past, construction of a home or building took six months or more, often allowing the wood to naturally dry out over time and reach a stabilized moisture content corresponding with the geographic region, typically less than 15%. It is known that for every 4% of moisture removed from the wood, a corresponding 1% of shrinkage of the wood occurs. Today, buildings and homes are often constructed in three to four months. This is insufficient time to achieve the dimensional stability and drying of the frames. Kiln dried wood, which is wood that has been previously dried in a kiln for 24-48 hours at temperatures between 170°-240° before being used in construction, is commonly being used to meet the fast construction deadlines. However, the cost of kiln-dried lumber ranges from $0.24-$0.30 per board foot, adding an additional $4,000-$5,000 additional lumber cost for a typical 2,000 square foot structure. Similar problems arising from TCA are known to exist in the food and shipping industries.

Accordingly, there is a need for a system and method for killing and removing biological organisms and reducing odors and volatile organic compounds in enclosures such as commercial and residential buildings, boats, vehicles and portable containers. Such a method should be non-toxic and performed in a relatively short amount of time. Such a method should also effectively kill and remove a large proportion of the dead organisms and substantially reduce volatile organic compounds. There is also a need for a method which can remove moisture from green lumber so as to speed up the construction process and eliminate mold and shrinkage concerns of framing which has too high of a moisture content. The present invention fulfills these needs and provides other related advantages.

SUMMARY OF THE INVENTION

The present invention resides in a process for removing or treating harmful biological and chemical substances from an enclosure, such as a building or vehicle by using heated air. The method of the present invention is non-toxic and can be performed in a relatively short amount of time while effectively killing and removing a large proportion of dead organisms, and substantially reducing volatile organic compounds and other dangerous substances, such as Mercury.

In one embodiment, a method for destroying, removing and/or denaturing harmful microbiological organisms and chemical substances from an enclosure includes the creation of a negative pressure within the enclosure. A manometer may be positioned within the enclosure to measure the pressure therein. If desired, the contaminated portion of the enclosure is physically cleaned or isolated before beginning the process.

Ambient air within the enclosure is then heated to a temperature between 110° F. and 400° F. This may be done by placing and distributing air into the enclosure using a heater passing heated air through a duct into the structure. Alternatively, a heating device, such as an electric heater or liquid-to-air heat exchanger device can be placed within the enclosure. A plurality of temperature probes may be positioned at predetermined locations relative to the enclosure to monitor the temperature in the enclosure until the predetermined temperature is achieved.

Heat sensitive articles may either be removed from the enclosure or protected, such as by insulated mats and the like. Moisture can be introduced into the heated air, such as by a humidifier; or moisture removed from the heated air, such as using a de-humidifier, as needed.

The pressure and elevated temperature increases the volatilization or vapor pressure of the chemical substances causing them to migrate into the ambient air. This also kills the harmful microbiological organisms. Preferably, the air within the enclosure is aggressively moved, such as by using blowers or fans, so as to facilitate the volatilization of the microbiological organisms and chemical substances into the air. Such chemical substances can include volatile organic compounds, oil, or chloroanisole compounds. Microbiological organisms killed by the process of the present invention include fungi, molds, viruses or bacteria. The blowers and fans also improve heating of the enclosure.

The biological organisms and chemical substances may be removed from the heated air by either incinerating them, or passing the heated air from the enclosure through a filter adapted to capture the microbiological organisms and chemical substances. Levels of volatilized chemical substances in the heated air may be monitored, such as by using a gas chromatograph device.

Non-heated ambient air may be directed into the enclosure after a predetermined time of directing heated air into the enclosure, while continuing to remove the air through the filter. Contaminated portions of the enclosure may be physically cleaned at the end of the process as well.

In another embodiment of the present invention, a method for destroying and/or denaturing biological organisms or removing chemical substances from a room of a non-tented building is provided. This includes placing a heating device, such as an oil heater, electric heater or liquid-to-air heat exchanger within the room of the building. Heat sensitive articles within the room are removed or protected. A plurality of temperature and/or moisture probes may be positioned at predetermined locations relative to the room to monitor the temperature in the room until a predetermined temperature is achieved. A positive pressure is created within the room, and the heating device heats the ambient air within the room to a predetermined temperature of between 110° F. and 400° F. to kill the organisms within the room, or cause the chemicals to volatize and migrate into the heated ambient air. Moisture may be introduced into the heated air if it is determined that it will facilitate the process.

Depending upon the nature or concentration of the chemical substances or organisms to be removed, the heated air may be passed through a filter adapted to capture the organisms and chemical substances. Preferably, the air within the room is aggressively moved to facilitate the volatization of microbiological organisms and chemical substances into the air.

In addition to the chemical substances and microbiological organisms mentioned above, this embodiment can be used to kill and remove other pests such as bed bugs or fleas. For example, the present invention can be used to kill bed bug insects in a portion of a multi-unit building. The portion may be a room and adjacent rooms of a hotel or the like. First, it is determined which discreet portion of the multi-unit building is infested with the bed bug insects. Ambient air within the infested discreet portion or room is then heated to a predetermined temperature of between 110° F. and 400° F. for sufficient time to kill the bed bug insects. Preferably, at least the infested room and the rooms adjacent to it, totaling less than all the rooms of the hotel, are treated with the heated air. Temperature probes are positioned as necessary, such as in a bed of the infested room to monitor the temperature. Heat-sensitive articles may be protected or removed from the infested area. Afterwards, the discreet portion or infested room is cleaned to remove the killed bed bugs. The bed bug entry points are then determined and sealed.

The present invention can also be used to remove pests from a structure, such as rodents, scorpions, birds, bats, etc. Ambient air within the structure is heated to a predetermined temperature between 120° F. and 400° F. to either kill the pests or drive the pests from the structure. This can be done by using a heater device, such as an electric space heater or liquid-to-air heat exchanger device, placed within the structure. Alternatively, a heater may pass heated air through a duct into the structure, or recirculated heated air may be used. A plurality of temperature probes may be positioned at predetermined locations relative to the structure to monitor the temperature in the structure until the predetermined temperature is achieved.

When the pests are insects, such as scorpions and other arachnoids, crevices may be sprayed with silica air gel before the structure is heated to weaken the pests. The pests may also be attracted to a selected location within the structure, such as by placing bait or the like. In this manner, a selected portion of the structure may be treated. A thermal imaging device is then used to determine pest access points into the structure. These access points are then sealed to prevent further intrusion.

In another embodiment of the present invention, moisture is removed from building materials of a partially constructed building. This is done by heating ambient air within the partially constructed building to cause moisture from the building materials to migrate into the heated ambient air. The heated air is then removed from the building. In some instances, the building must be enclosed, such as with tenting or the like. A dehumidifier may also be placed in the building to remove the moisture from the heated air. Typically, the air is heated using a heater placed within the building, although heated air may be introduced through a duct into the building. Temperature probes at predetermined locations within the building monitor the temperature until a predetermined temperature is achieved. Additionally, humidity or moisture probes may be provided for monitoring moisture in the structure or air during the treatment process.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings for purpose of illustration, the present invention is related to a system and method for treating buildings and enclosures. In accordance with the present invention, heating of the air is primarily used to treat such enclosures and buildings so as to remove and/or denature harmful organic substances, such as VOCs, microbiological agents such as bacteria and viruses, and pests such as bed bugs, scorpions, etc. and their allergens from an enclosure.

Figure 1:
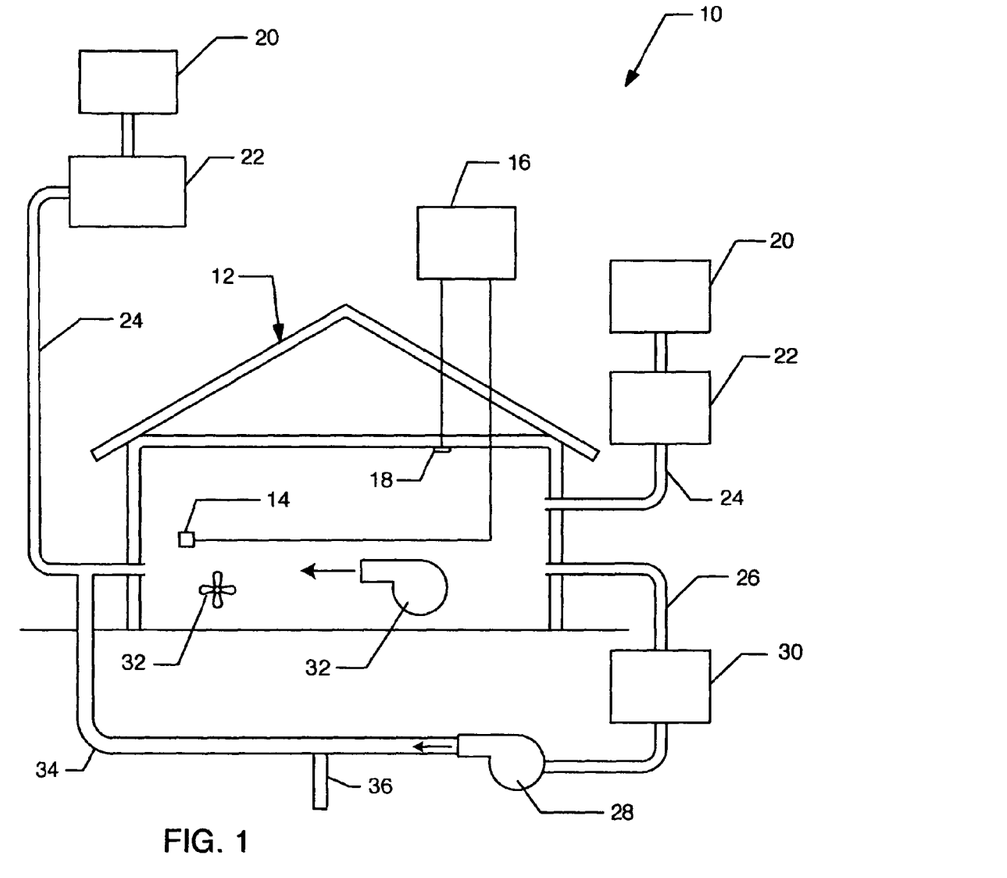
FIG. 1 is a schematic diagram showing various components of the system of the present invention installed for treatment of a building.

Referring now to FIG. 1, there is seen a schematic diagram showing the components of the system of the present invention, referred to generally by the reference number 10, in use treating an enclosed structure 12. The enclosed structure 12 is typically a commercial or residential building, but can also be a vehicle, such as an airplane, bus, boat, automobile, etc.

A plurality of temperature sensors 14 are positioned at predetermined locations within the structure to monitor the temperature of the structure 12. Typically, these sensors 14 have thin, elongated tips that can be adhered to or pushed into materials to be heated or into suitably sized holes drilled into such materials so as to measure the surface and/or internal temperature. The sensors 14 may be wired to a console 16 which displays and records the temperature at each sensor 16 in real time. Alternatively, the sensors 14 may be wireless and transmit a signal to the console 16. Typical sensors 14, as by way of example and not by way of limiting, include thermal couples, thermistors, or the like connected to a computer and/or a strip chart recorder console 16.

A pressure measuring device, such as a manometer 18, is positioned within the structure 12 so as to measure the internal pressure of the structure 12 during operation of the invention. As will be more fully described herein, in some instances, positive air pressure is desirable. However, in most instances, a negative pressure is established and maintained throughout the operation of the method of the present invention in order to prevent the dispersal of harmful biological and organic contaminants throughout the structure 12. The manometer 18 can be linked to the console 16 to provide the pressure information from without the structure 12.

One or more heaters 20 heat air to a predetermined temperature lethal to the organisms to be destroyed. For a more complete disinfection, the air temperature is preferably raised to at least about 155° F., with optimum results generally achieved with temperatures in the range of about 110° F. to 400° F., or higher. A biocide, having desirable characteristics enhanced by heat, may be added to or removed from the heated air to facilitate the destruction and removal of the chemicals and microbiological organisms. Moisture may also be added to or removed from the heated air to facilitate the destruction and removal of the chemicals and microbiological organisms.

Any suitable heater 20 may be used. A gas burning heating device 20, such as a conventional propane heater, is preferred as being particularly efficient in heating air. Any other heating arrangement, such as oil heaters, electrical devices, solar heaters, and light emitting devices, may be used if desired, as will be more fully discussed and illustrated herein.

Heated air (and biocide, if used) from the one or more heaters 20 is directed through blower 22 (which may, if desired, be a component of the heater 20) which injects the hot air into the enclosed structure 12 through at least one inlet duct 24. Generally, a plurality of inlet ducts 24 will be used to achieve the optimum distribution of hot air throughout the enclosed structure 12. The inlet ducts 24 preferably include variable flow dampers and may be moved while the system is in operation to achieve uniform temperatures in all areas of the structure being treated, as sensed by sensors 14 and observed at console 16.

At least one outlet duct 26 is provided to allow the air to be removed from the structure 12. A blower or vacuum 28 is connected to the outlet duct 26 in order to remove air from the interior of the structure 12. Vacuum 28 may be used to create a negative pressure within the structure 12. Typically, this negative pressure is created before the heated air is introduced into the structure 12. The removed air is filtered, typically utilizing a high particulate arrestance filter, ULPA filter, or the like coupled with the vacuum/blower 28. Other filters such as charcoal filters or UV filters may be employed as well. Additionally, or alternatively, the air which is removed from the structure may be heated to very high temperatures so as to incinerate or otherwise neutralize the potentially harmful chemicals and microbiological organisms which have volatilized into the air. The filter or air scrubber 30 removes the remains of the organisms and VOCs from the air to prevent them from reaching the environment or being re-introduced into the structure 12.

Preferably, additional blowers 32 or fans are positioned within the structure 12 to aggressively move the air within the structure to further enhance the removal of harmful biological and organic substances by volatilizing the microbiological and chemical substances and aid in heat distribution.

Additionally, fans 32 may be positioned strategically within the structure 12 to selectively move the air away from predetermined heat-sensitive articles or areas of the structure in which such an elevated temperature is not desired. Typically, however, such heat-sensitive articles are removed from the structure or covered with insulation mats or the like.

In a particularly preferred embodiment, the filtered air is re-directed through duct 34 into the structure 12, such as by linking duct 34 with inlet 24. Such re-circulation of heated air enhances the energy and thermal efficiency of the process and decreases the overall treatment time. Recirculating has been found to increase air circulation within the containment area of the structure 12. The re-circulated air may be blended with the heat processed air as it exits the heater, re-heated by the heater 20 or simply re-introduced by way of ducting into the structure 12.

It will be appreciated by those skilled in the art that the present invention, as described above, can be used in a variety of scenarios. For example, in the event a building is infected with viruses or bacteria, such as a hospital, an individual's house which has been contaminated with a lethal virus or bacteria, an office building which has been exposed to bio-terrorism or the like. The building may be simply de-gassed to remove VOCs and reduce the potential for SBS in the employees or occupants thereof. In such instances, when a dangerous chemical or microorganism is being removed from the enclosure, it will be appreciated that they cannot be simply released into the atmosphere. Instead, the filters and incinerators must be used to destroy, neutralize and contain these organisms and substances and prevent their release into the environment. However, in other cases, venting to the atmosphere is possible, such as when removing VOCs and the like.

The present invention, as described above, can also have various other specific applications. For example, in the northeastern portions of the United States, fuel oil is typically used to heat homes and other structures. Often, spills occur during the fueling process. These fuels are difficult to clean, and sometimes the fuel oil penetrates into building components. The present invention can volatilize and remove these spills.

As mentioned above, TCA residue left over from the cleaning process and interacting with mold in corks and the like is a tremendous problem in the wine industry. Structures can be heated and treated, in accordance with the present invention to volatilize this chemical from wine making facilities. Of course, the present invention will also kill the mold, and remove released spores and the like.

The removed air can be sampled in order to determine if the level of contaminants in the heated air. For example, an outlet 36 may be installed in the ducting 34 or 26, and a gas chromatograph or a like device can be used to determine the levels of the contaminants before, during and after the heating process of the invention. This can be used in determining the period of time necessary to treat the structure. When the contaminants, such as VOCs has fallen below acceptable limits, the process can be terminated.

Figure 2:
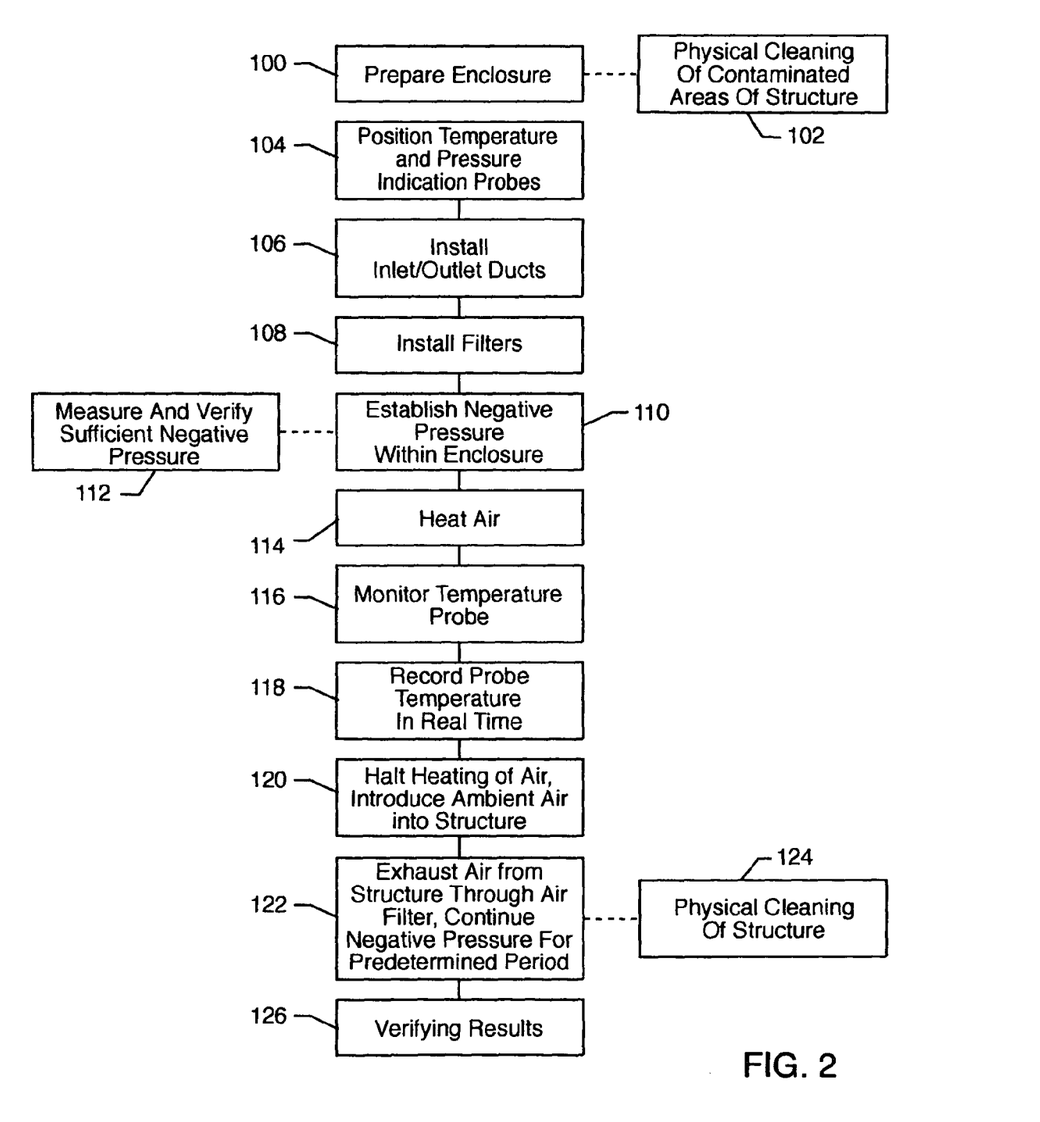
FIG. 2 is a flow-diagram illustrating the steps taken in the method of the present invention.

With reference to FIG. 2, in the operation of the system of the invention, the first step is to prepare the structure, as indicated in block (100). This basically involves removing all heat-sensitive items from the enclosure or, in some cases, covering heat sensitive items, such as electronic devices and plastic items, with thermal insulation material. All material that has a flash/melt point at or below the maximum temperature to be used (such as candles, lipstick, etc.) must be removed.

Typically, the preparation of the structure also includes physical cleaning of contaminated areas of the structure (102), which may be preformed while the area is under a negative pressure. This can include vacuuming, wiping, scraping, etc. of various surfaces which have been contaminated with harmful biological contaminants, such as mold, fungi or bird, rodent or insect debris, etc. In extreme cases, this may require the removal of carpeting, section of walls, etc. However, the invention is intended to neutralize and remove these biological and chemical contaminants without requiring resort to such extreme measures in most instances.

In one embodiment, particularly when treating the structure 12 for mold and fungi, biocides and preferably boric acid, are dispersed within the structure 12 at locations, preferably, where mold and fungi are likely to be encountered. Boric acid, $H_3BO_3$, is a white crystalline, oxygen-bearing acid of boron found in certain minerals and volcanic waters or hot springs in certain mineral deposits. Boric acid, or salts of boric acid, borates, traces of boron are necessary for growth of land plants and thus are indirectly essential for human life. In excessive quantities, however, borates may act as unselective herbicides. The most common source of boric acid is borate, sodium tetra borate or borax, which occurs naturally in salt beds. Boric acid may be obtained by treating borate with sulfuric acid. Boric acid is commonly used as a mild antiseptic for burns and surface wounds and comprises a major ingredient in eye lotions. Importantly, boric acid is non-toxic to humans and animals and is ecologically benign in low concentrations.

Applying boric acid using conventional applicator methods and devices, i.e., dusting boric acid as a conventional insecticide as dust, spraying a solution or slurry or dispersion of boric acid, etc., coupled with heating the air within the enclosure, advantageously improves mold, fungi and pest abatement within the structure 12. The borates may be used in pre-treating contents of an enclosure, such as building materials, lumber, etc. or in post-treating such contents after application of heat.

A plurality of temperature indicating and pressure measuring probes 14 and 18 are placed in predetermined locations as indicated in block (104) to assure that the required temperature levels are achieved. In some cases the probes 14 can be read directly, although preferably they are connected by wires or wireless means to the console 16, so that all probes 14 and 18 can be monitored conveniently and the data recorded in real time.

The enclosed structure 12 may be sealed and at least one inlet duct 24 and at least one outlet duct 26 installed as indicated in block (106). Generally, a plurality of inlet ducts 24 is preferred. Although each duct 24 may enter the enclosed structure 12 separately, the use of one inlet duct 24 connected to a manifold from which plural ducts extend to predetermined locations within the enclosed structure 12 is preferred. Ducts 24 may enter the structure 12 through any suitable opening, such as an open window or door with the remainder of the window or door blocked by a panel. In some instances, such as when treating vehicles, tenting may actually be required or desired to treat the structure 12. However, in most instances such tenting is not required.

The appropriate air scrubbing filters 30 and vacuum devices 28 for facilitating the removal of the heated air and filtering the harmful substances therefrom, are installed, as indicated in block (108).

When the components of the system 10 have been properly prepared and positioned, heated air is directed into the inlet ducts (110). The desired pressure is established within the structure 12 (112) and the manometer or other pressure sensing device is used to verify that a sufficient pressure is present. In some instances, a positive pressure is actually desired wherein the ingress of heated air flow into the containment area exceeds the egress air flow from the negative air machines 28. Such positive pressure may be desired to force the contaminants to volatize or otherwise enter the circulated air. Typically, a negative air pressure within the structure 12 is desirable, by removing air more quickly than it is introduced, to ensure the removable of the contaminants therefrom and to promote circulation of the air. This is accomplished using the vacuum/blower device 28 and filter 30 as described above. Using the pressure measuring manometer device 18, the internal pressure of the structure is measured and it is verified that sufficient negative pressure is present. Often the establishment of negative pressure is performed before any heat is introduced into the structure in order to begin the removal of any loose and aerosolized contaminants, and prevent their sporulation before heat is introduced.

The heated air is then introduced into the structure (114). Flow of the heated air through the enclosed structure 12 may range in time from a few hours to several days to provide optimum results. During this time, the temperature probes 14 are monitored (116) and these results recorded in real time (118) to ensure that the intended areas within the structure 12 are properly treated.

The heated air which has been circulated through the structure 12 is preferably continually removed through an air scrubber filter to remove the remains of the destroyed microorganisms and chemicals, such as VOCs. Biocides, such as ozone or even moisture, may be added to the heated air to enhance the treatment effect.

At any time during system operation, the inlet and outlet ducts 24 and 26 may be moved to assure uniform temperatures throughout the structure, as indicated by the temperature probes 14 and temperature monitoring console 16.

After a predetermined period of time in which it has been determined that the harmful biological organisms and agents have been destroyed, the heating of air is halted and non-heated ambient air may be introduced into the structure (120). The air from the structure is then exhausted through the air filter while the negative pressure is maintained for a predetermined period of time (122). These steps are taken in order to prevent any viable fungi, molds, etc. from sporulating or the like as such organisms when threatened with destruction will often sporulate or form cysts or the like to facilitate the survival of the organisms and their progeny. The aggressive air flow through the structure continues to remove the harmful microorganisms, chemical substances, etc., for some time.

This entire process may often be completed in as little as one to twelve hours, for example, allowing a business to be closed for only one day or a residential structure to be fully treated during a typical work or school day. However, in certain circumstances, such as in the case of large structures or high levels of harmful substances within the structure, the process may be extended to several days or more to ensure that the structure is properly treated. It has been found that while harmful organisms are killed and removed during this process, the reduction of the VOCs actually continues for some time after treatment. Placing a filtering system within the structure and/or opening a window to allow the structure 12 to properly vent is believed to be adequate to remove these residual compounds.

In certain instances, the structure 12 is then physically cleaned (124) after the aforementioned steps have been performed. For example, when dealing with the Hanta virus, the health concerns of the workers dictate that the virus be killed and removed to the greatest extent possible. Then, after the virus has been destroyed and removed to the greatest extent possible utilizing the aforementioned steps, workers can enter the structure and physically remove rodent droppings and the like which may contain the neutralized viruses. Samples and specimens may be taken of the previously contaminated areas to verify the desired results (126) and a physical examination of the structure can be used to verify the removal of the contagions and harmful substances. The sampling of the air, while heated or when cooler ambient air is introduced and removed, can also be used to verify the results using a high speed gas chromatograph device or the like.

Although the above description has been directed to rather large structures, such as residential or commercial buildings and passenger occupiable vehicles and the like, the present invention can also be applied to treatment of much smaller areas or objects. For example, a single room of a building may be treated by sealing the windows, doors, and other passageways of that particular room or area and treating such area, as described above. There are also instances where small personal articles, such as clothing or bedding, or even furniture is required to be treated, or a portion of the structure, but not the entire structure itself.

Figure 3:
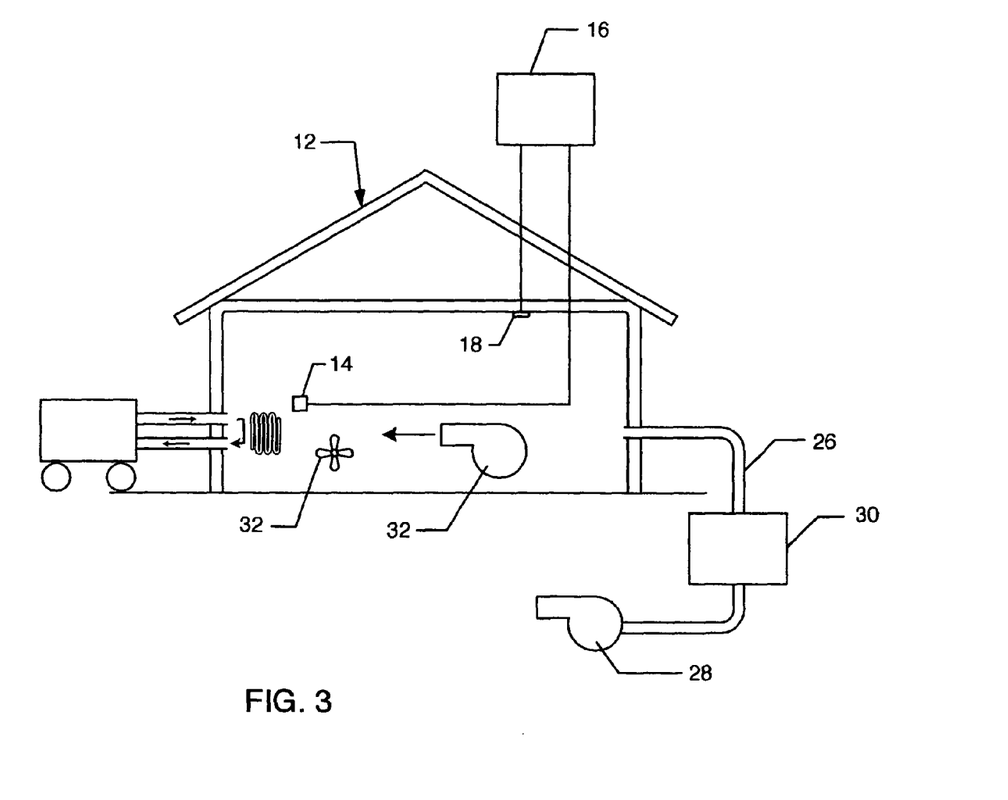
FIG. 3 is a schematic diagram showing various components of another embodiment of the present invention, installed for treatment of a building.

With reference now to FIG. 3, another embodiment of the invention is illustrated which is similar to that described above. However, instead of using an external heater, such as a propane gas tank heater, with inlet ducts, this embodiment utilizes a liquid-to-air heat exchanger device 38 disposed within the enclosure. A heating device 40, preferably a device which is movable or placed on a trailer or the like, heats a liquid, such as water, oil, etc. The heated liquid is then transferred via an inlet conduit 42 into the heat exchanger device 38. Radiator-like fins, fans, etc. can be used to force air over the heat exchanger 38 and cause the air to be heated as it comes into contact with the exterior surfaces of the heat exchanger 38. The now cooler liquid is then returned to the heater 40 through an outlet conduit 44. The conduits 42 and 44 can be linked to multiple heat exchangers 38, or multiple inlet and outlet conduits 42 and 44 can extend from the heater 40 to each heat exchanger 38 so as to sufficiently heat the air within the structure 12. A benefit of this embodiment is that the preparation of the structure 12 is minimized by eliminating the need for ducts and the like. As previously described, however, the system still preferably includes blowers or fans 32 for aggressively moving the air within the structure 12, temperature probes and pressure sensors 18 and 14, as necessary, for monitoring the appropriate temperatures and desired pressure.

As discussed above, when treating structures 12 having dangerous micro-organisms or chemical substances, a negative pressure can be created with a blower 28 attached to an outlet vent 26. An incinerator or filter 30 can be used to neutralize and destroy these organisms and substances as they are pulled from the structure 12. It will be understood, however, that in other instances there is no need for an outlet duct or conduit 26, filter 30 and blower 28. Instead, a positive pressure is built up within the structures 12 due to the heating of the air by the heat exchanger 38, and the aggressive movement of the air by the blowers and fans 32. In this case, an outlet in the form of an open window or the like can be used to exhaust the heated air from the structure 12.

Figure 4:
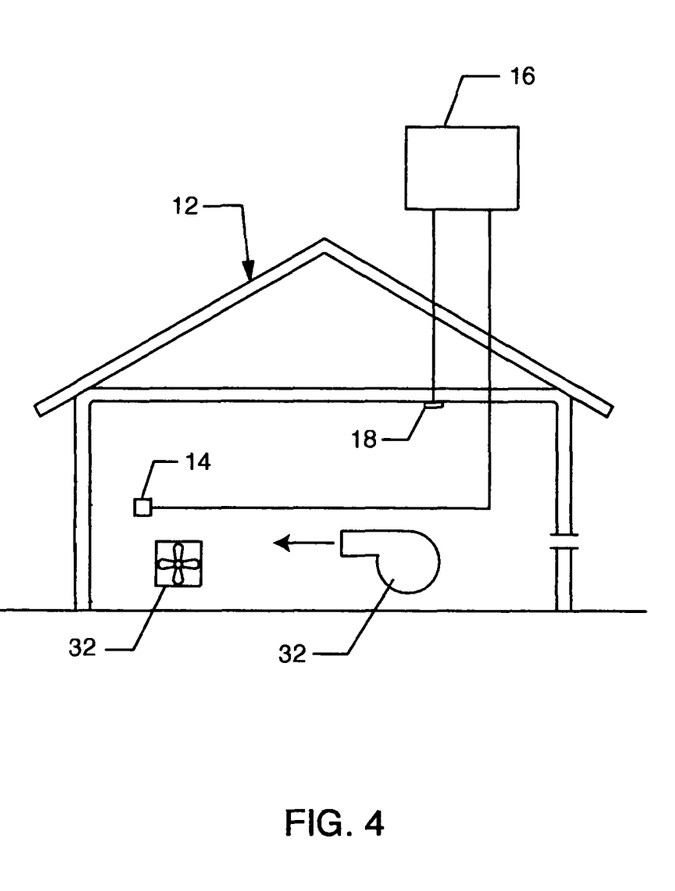
FIG. 4 is a schematic diagram showing components of another embodiment of the present invention, installed for treatment of a building.

With reference now to FIG. 4, yet another embodiment is shown which is similar to that of FIG. 3. However, instead of a heat exchanger device 38, this embodiment utilizes an electric space heater 46. In this case, one or more electric heaters 46 are selectively positioned within the structure 12 and serve to heat the air therein. Blowers and fans 32 or the like can be used to aggressively move the air past the heating coils of the heater 46 to heat the air, as well as volatilize certain chemicals into the air. By increasing the temperature, and the air movement, the vapor pressure is increased. By increasing vapor pressure, certain chemicals can be volatilized into the air and removed from the building structure 12 and other fixtures or components within the building. The pressure and temperature sensors 14 and 18 are used and connected to a console 16 or otherwise monitored to ensure either the proper negative or positive pressure, as well as the proper temperature range needed for the particular structure 12. In the embodiment illustrated in FIG. 4, there is no outlet duct or conduit or filter. Instead, the outlet 48 is an opening in the structure 12, such as an open door, window, etc. It will be appreciated by those skilled in the art that this presents a significant labor savings when preparing the structure.

Nonetheless, in the embodiments illustrated in FIGS. 3 and 4, with the heat exchanger device 38 and internally placed electric heater 46, any number of the steps and components illustrated and described with respect to FIGS. 1 and 2 can be implemented, as needed. Thus, the entire structure 12 can be sealed and inlet and outlet ducts incorporated. Either positive or negative pressure can be utilized. When dealing with harmful substances, a negative pressure and filter or incinerator 30 are used. However, in many cases, the doors and windows of the building can be closed and sealed the building sufficiently to create an enclosure whereby the air can be heated to the necessary temperature to either kill the micro-organisms, pests, or cause the chemical substances to be released into the heated air for removal. In some instances, certain areas of the structure 12 will be cleaned and pre-treated, such as by applying a biocide (such as boric acid, or the like) scraping and removing sections of walls or flooring having toxic mold and the like, etc. In other cases, these steps may not be necessary. In some cases, the air within the structure 12 need only be heated to between 110° F. to 150° F. However, in other cases, the required temperatures are much higher, such as 200° F. to 400° F.

Figure 5:
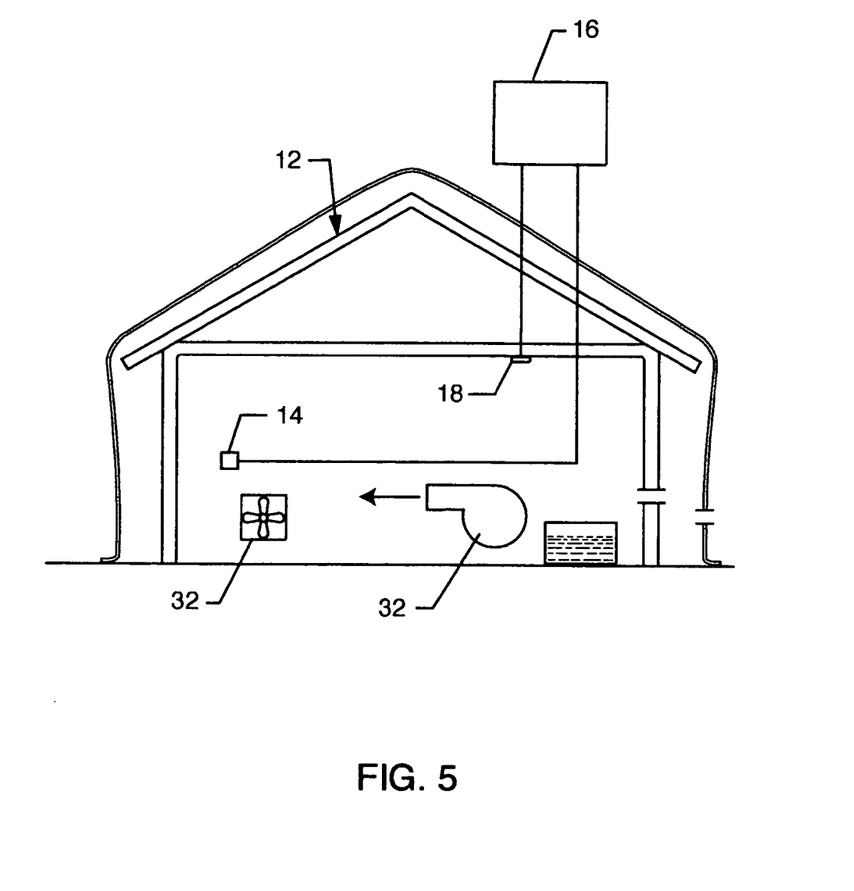
FIG. 5 is a schematic diagram showing various components of the present invention installed for removing moisture from a partially constructed building, in accordance with the present invention.

With reference now to FIG. 5, the method of the present invention can be advantageously used to dry building materials of a partially constructed building, such as the illustrated structure 12. Typically, the present invention is performed after the framing process when the wooden framing structures have been installed in the building, but before drywall, paint, carpeting and the like are installed. Preferably, the roof 50 of the structure has already been constructed. Additionally, preferably the outer brick, stucco, etc. is also present, but is not required. The least partially finished roof and exterior can create a sufficient enclosure for the purposes of this embodiment. However, in other instances, such as when the exterior or roof is not completed, a tent 52, comprised of tarps or the like, is extended around the partially constructed building 12 so as to substantially enclose it.

The necessary components are installed, such as illustrated internal electric heater 46 (although other heating methods can be employed such as the previously described heat exchanger 38 and exterior heater with inlet ducts). Probes such as temperature probes 18 and the like are preferably used and linked to a console 16. Blowers and fans 32 can be used to aggressively move the heated air within the partially constructed building 12 so as to evenly disburse the heated air, and create a positive pressure such that the heated air will exit the building through an opening 48, such as an open window or unfinished opening, and an opening in the tarp tent structure 54.

As discussed above, lumber that has too high a moisture content can lead to mold colonization, odors, shrinkage resulting in drywall problems, and ultimately potential health and legal issues to the builder. Lumber that is wet during the framing stages, whether it arrives wet or becomes wet at the job site, is a problem if it is not allowed the time to dry. With the requirements to build homes quickly, the moisture problem may not be adequately addressed.

In lieu of the purchase of expensive kiln-dried lumber, the present invention can be used to improve the quality of homes and buildings produced and at a lower cost, with decreased quality problems, warranty costs, and construction defect lawsuits.

The ambient air within the building 12 is heated to above ordinary atmosphere temperatures such as between 100° F. and 200° F. The air conveys the heat to the wood and carries away evaporated moisture. Lumber dries from the outside to the inside. Water is contained in wood cells in two ways. The first level of moisture in wood is found in the cell cavity as "free" water. The second level is water absorbed in the cell wall as "bound" water. Green lumber is defined as having the cell wall saturated and a variable amount of liquid or "free" water in the cell cavities. Once all the "free" water has been removed from the wood and the cell walls remain fully saturated, the lumber is at the "fiber saturation point". Stated in terms of moisture content, green lumber typically exceeds 25% to 30% moisture content. A reduction of moisture content from the fiber saturation point occurs as the "bound" water is removed from the cell walls. The wood begins to experience shrinkage and the wood strength begins to increase. The process of drying in accordance with the present invention allows the wood to reach moisture equilibrium with the surrounding atmosphere, typically less than 15% moisture content.

Over the period of only a few days, the desired moisture removal can take place using the method of the present invention. Devices such as de-humidifiers 56 or the like can be used to remove moisture from the heated air to facilitate the process. Once the proper moisture content has been achieved, the overall frame structure has increased dimensional stability as the frame will not experience significant shrinkage or swelling, and their attendant problems. Fungal attacks will generally not occur in dry wood. If the wood used for framing happens to include any insects or larvae, such as dry wood termites or beetles, these insects will most likely be destroyed. The framing is further enhanced for additional treatment, such as gluing, application of fire retardants and paints, etc. The same process can be utilized during the mudding process during drywall installation to facilitate the drying of the drywall mud such that the interior can be painted more quickly.

Figure 6:
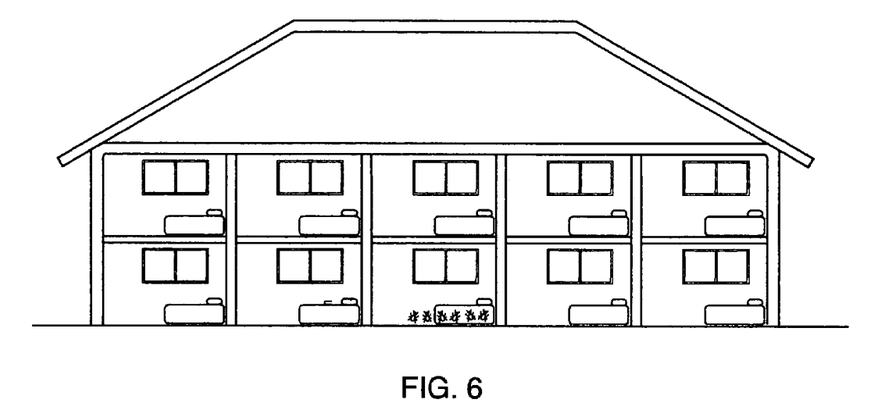
FIG. 6 is a schematic diagram of a multi-unit building having at least one room infested with pests, such as bed bugs.
Figure 7:
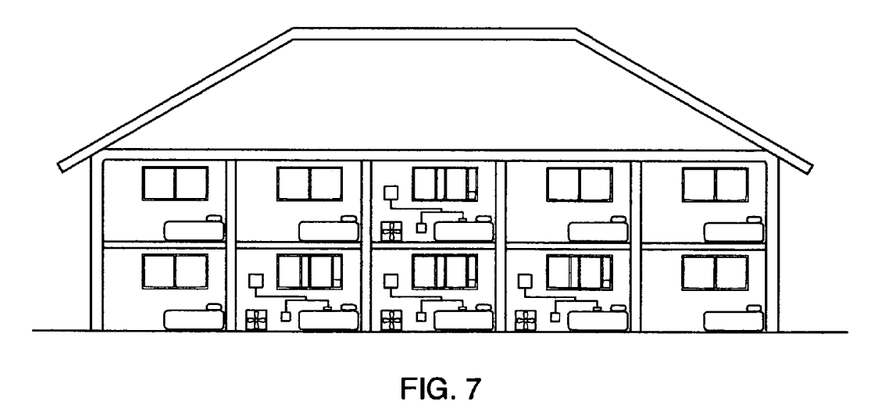
FIG. 7 is a schematic diagram similar to FIG. 6, showing various components of the present invention installed for treatment of the pest infestation in one or more rooms of the multi-unit building.

With reference now to FIGS. 6 and 7, there currently exists a significant problem with pests, in particular fleas, head lice or bed bugs 58, infesting a room 60 of a multi-unit building 62, such as a hotel or apartment building. Pests such as fleas and head lice can be introduced by the individual staying in the room 60 or their pets. Bed bugs, blood-sucking parasites, can be introduced in a variety of ways, such as birds or bats nesting in the eves of the building 62, etc. These bugs 58 find their way through cracks and crevices in the building and aggressively pursue hosts, such as sleeping humans. As discussed above, bed bugs hide in cracks and crevices during the day and come out at night to feed. Such bugs are not limited to the bed, but can be found in stuffed furniture, behind loose wallpaper, under carpet, behind picture frames and in electrical outlets, etc. Thus, merely cleaning or destroying the bed or bedding will not resolve the problem. Fumigating presents many drawbacks, particularly in a hotel setting. Although the entire building 62 could be treated, this presents a serious financial drawback for the several days in which the building must be prepared and treated.

Accordingly, the present invention can be used to treat a single room 60, or its adjacent rooms, as illustrated in FIG. 7, to eradicate the pests. The room 60 is prepared by placing temperature probes 14 at selected locations within the room 60, such as between the mattresses of the bed 64, and other known bed bug harborages, including under cushions, stuffed furniture, under carpeting, etc. Heaters 46 are disposed within the room or the necessary ducting is implemented. A console 16 or the like can be used to monitor the operation of the temperature probe 14 and heater 46, as necessary.

Prior to heat treatment, cracks and crevices and other bed bug harborage areas can be dusted with diatomaceous earth or silica aerogel, which can adversely affect the cuticle or exoskeleton of the bugs and make them more susceptible to heat treatment. The room 60 is then heated to a predetermined temperature, such as 140° F., for the necessary time. Three hours at this temperature typically kills the bed bugs 58. Although the bed bugs may only be known to be present in one room, such as when a hotel guest complains of bed bug bites, it is most desirable that the rooms 66-70 surrounding the infested room 60 also be treated. This is due to the fact that bed bugs and other insect pests can crawl through crevices, along electrical lines, etc., to reach areas of lower temperature and safety. Thus, if the heaters 46 are disposed in the adjacent room 66-70, so as to heat these rooms as well, the bed bugs 58 will be destroyed, even if crawling along plumbing lines, electrical lines, air ducts, etc. However, this still enables the selective treatment of as few as a single room, and perhaps as many as four to six rooms of the entire hotel or apartment complex to completely eradicate the bed bugs.

After treatment, all crack, crevices, mattresses, etc., are vacuumed and inspected to remove the dead bed bugs and eggs. The cracks and crevices are then sealed, such as using caulking material or the like, to prevent future infestation.

Although the rooms can be sealed, and inlet and outlet ducts provided, as described with respect to FIGS. 1 and 2, due to the relatively lower temperatures (130° F.-140° F.) and the non-toxic nature of the killed insects, the rooms need relatively little preparation other than the closing of windows and sealing of door jambs and the like and the installation of the heater 46 and temperature probes 14. Once the method of the present invention has been used to eradicate the bed bugs, this can typically be done in less than one-day, with no toxic or adverse affects to future customers of the hotel or apartment.

Figure 8:
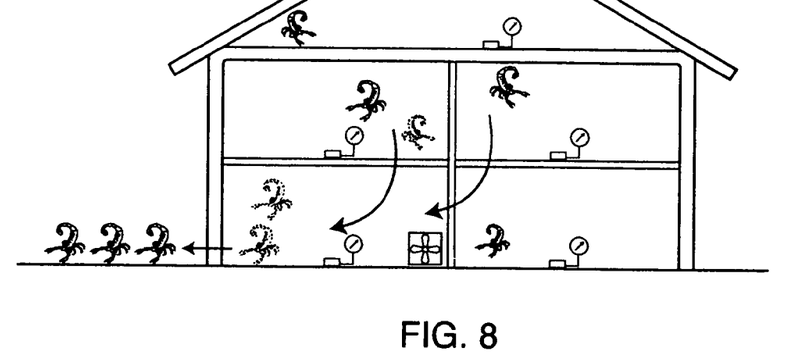
FIG. 8 is a schematic diagram showing various components of the present invention installed for treatment of a building infested with pests, such as scorpions, and the determination of an ingress/egress point in the building.
Figure 9:
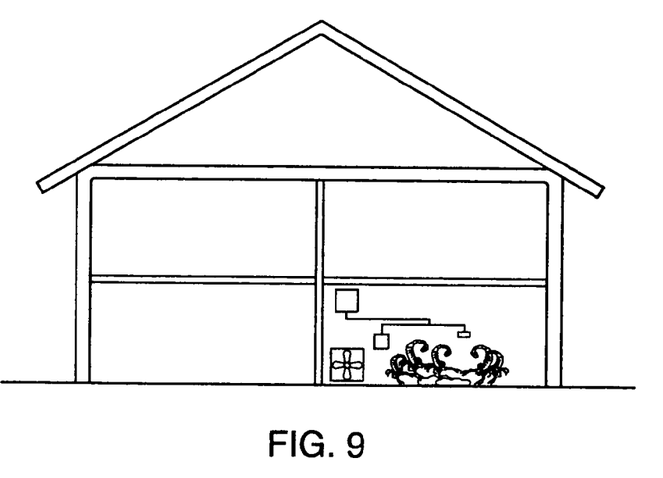
FIG. 9 is a schematic diagram showing various components of the present invention installed for treatment of pests in a single room of a building, where the pests have been drawn into that room, in accordance with the present invention.

With reference now to FIGS. 8 and 9, as described above, pests often find their way into buildings and dwellings 12. In particular, in certain southwest portions of the United States, an increasing problem is the infestation of scorpions 72 into houses and the like where the temperatures are cooler and additional moisture can be found. The incidences of scorpion stings to both humans and pets have increased as houses and buildings have been constructed in desert areas beyond the city boundaries. The present invention can be used to eradicate and remove these pests 72.

In one embodiment, as illustrated in FIG. 8, one or more heaters 46 are used to heat the entire structure 12. Temperature probes 14 are placed in selected locations within the structure 12. It will be appreciated that multiple inlet ducts may be used to import heated air, as discussed above. The air within the structure 12 is heated to a predetermined level which is lethal to the scorpions 72, or other pests. This can cause the scorpions 72 to die in Situ. Alternatively, the scorpions 72 find ingress/egress points 74 in the structure 12 and flee the structure 12. Thermal imaging devices, such as thermal imaging cameras and the like, can be used to detect the ingress/egress points 74, such as by viewing the scorpions or rodents 72 fleeing the structure 12, or more typically the heated air escaping from such points 74. These points can then be sealed by using caulking material and the like to prevent future infestation.

With reference now to FIG. 9, in another embodiment, the pests 72 can be attracted to one location within the structure 12, such as a single room 76, a garage, basement, etc., using an attractant 78. The attractant may comprise a bait in the case of rodents and the like, or a wet towel or rug. Scorpions 72 are attracted to the moisture in a wet towel or rug. Placement of the wet towel or rug in the desired room 76 can attract a scorpion 72 overnight. The next morning, the heater 46 can heat the air within the room 76 to kill or drive out the scorpions 72, as described above.

In yet another embodiment, the present invention can be used to treat non-processed food. For example, nut growers often experience the problem of insect infestation, such as meal worms and the like. This is particularly a problem in the pistachio industry where meal worms can infect the nuts, such as by boring a hole through the shell to feed on the nut inside.

Roasting the nuts at elevated temperatures for prolonged periods of time effectively kills such meal worms and other insects. However, many nuts are not roasted as this imparts a different taste and quality to the nut. Applying insecticides and other chemicals to the nuts preserves their non-roasted characteristics, but presents obvious health concerns.

Accordingly, the present invention is used to heat the nuts to a temperature sufficient to kill the meal worms or other insects which have infected the nuts, but at a temperature which is much lower than roasting temperatures, or for a period of time much less than roasting temperatures so that the nuts still have the non-roasted characteristics, flavor, etc. This can be done, for example, by passing the nuts on a conveyor system into an enclosure where the nuts are rapidly heated, and then subsequently cooled. Alternatively, the nuts can be placed in a heating room where they are heated at a relatively low temperature for a prolonged period of time, or an elevated temperature for a very short time followed by cooling. Whereas roasting temperatures are often in excess of 200° F., the temperature for killing these pests can be much lower, such as 120°-150°.

Although several embodiments have been described in detail for purposes of illustration, various modifications may be made to each without departing from the scope and spirit of the invention. Accordingly, the invention is not to be limited, except as by the appended claims.

What is claimed is:

1. A method for sanitizing a structure of pests including insects, comprising the steps of:
    heating ambient air within the structure to a temperature of between 100° F. and 400° F. to either kill the pests or drive the pests from the structure;
    using a wireless temperature sensor to determine heat leakage points from the structure; and
    dusting at least a portion of the structure with silica or diatomaceous earth.

2. The method of claim 1, including the step of attracting the pests to a selected location within the structure.

3. The method of claim 2, wherein the attracting step includes the step of placing bait within the selected location of the structure.

4. The method of claim 1, wherein the heating step includes the step of distributing heated air into the structure using a heater passing heated air through a duct into the structure.

5. The method of claim 1, wherein the heating step includes the step of placing a heater device within the structure.

6. The method of claim 1, including the step of positioning one or more of temperature or moisture probes at locations to monitor the temperature in the structure until the temperature of between 100° F. and 400° F. is achieved.

7. The method of claim 1, including the step of dispersing a biocide within the structure prior to or after the heating step.

8. The method of claim 7, wherein the biocide comprises boric acid.

9. The method of claim 1, wherein the pests further include rodents.

10. The method of claim 1, wherein the pests further include insects.

11. A method of claim 1, wherein the pests include bacteria, viruses, fungi or other pathogens.

12. The method of claim 11, wherein the wireless temperature sensor comprises a thermal imaging device.

13. The method of claim 1, including the step of sealing the heat leakage points in the structure.

14. The method of claim 1, including the step of utilizing chemicals to kill the pests within the structure.

\* \* \* \* \*